United States Patent
McDonald

(10) Patent No.: US 9,877,802 B2
(45) Date of Patent: Jan. 30, 2018

(54) CIRCUMFERENTIAL MATRIX BAND

(75) Inventor: Simon P. McDonald, Katikati (NZ)

(73) Assignee: Dentsply Sirona Inc., York, PA (US)

( * ) Notice: Subject to any disclaimer, the term of this patent is extended or adjusted under 35 U.S.C. 154(b) by 0 days.

(21) Appl. No.: 14/123,181

(22) PCT Filed: Jun. 11, 2012

(86) PCT No.: PCT/US2012/041928
§ 371 (c)(1),
(2), (4) Date: Mar. 17, 2014

(87) PCT Pub. No.: WO2012/171018
PCT Pub. Date: Dec. 13, 2012

(65) Prior Publication Data
US 2014/0199652 A1   Jul. 17, 2014

(30) Foreign Application Priority Data

Jun. 9, 2011 (NZ) .................................... 593353
Oct. 10, 2011 (NZ) .................................... 595654
Nov. 3, 2011 (NZ) .................................... 596177

(51) Int. Cl.
*A61C 5/04* (2006.01)
*A61C 5/12* (2006.01)
*A61C 5/85* (2017.01)

(52) U.S. Cl.
CPC ............ *A61C 5/125* (2013.01); *A61C 5/85* (2017.02)

(58) Field of Classification Search
CPC ........... A61C 5/04; A61C 5/125; A61C 5/127; A61C 5/122; A61C 19/003
(Continued)

(56) References Cited

U.S. PATENT DOCUMENTS 2,588,059 A   3/1952   Tofflemire
3,046,659 A   7/1962   Tofflemire
(Continued)

FOREIGN PATENT DOCUMENTS

DE   1056323   4/1959
EP   2353541   8/2011
FR   2598076   11/1987

OTHER PUBLICATIONS

International Search Report, PCT/US2012/041928, International Searching Authority: European Patent Office, Authorized officer: Herve, Chabus, dated Aug. 29, 2012.

*Primary Examiner* — Matthew Nelson
(74) *Attorney, Agent, or Firm* — Leana Levin; Douglas J. Hura; David A. Zdurne

(57) ABSTRACT

A dental matrix band includes a band having a first end and a second end. The band is folded over with the first end and second end generally aligned. A portion of the band adjacent the first and second ends form opposed facing band portions in contact with one another, and another portion of the band forming a looped band forming a circumference. A first or stationary toggle is secured to the band at the first and second ends with the first toggle stationary with respect to the band. A second or movable toggle is formed over the band and is capable of sliding over the opposed facing band portions in contact with one another, whereby sliding of the movable toggle away from the first and second ends causes the circumference of the looped band to reduce in size.

20 Claims, 2 Drawing Sheets

(58) Field of Classification Search
USPC .......................................... 433/39, 148–149
See application file for complete search history.

(56) References Cited

U.S. PATENT DOCUMENTS

| | | | | |
|---|---|---|---|---|
| 3,152,400 A | | 10/1964 | Lang | |
| 3,237,307 A | * | 3/1966 | Tofflemire | A61C 5/125 433/155 |
| 3,482,314 A | * | 12/1969 | Tofflemire | A61C 5/125 433/141 |
| 3,517,444 A | * | 6/1970 | Tofflemire | A61C 5/125 433/158 |
| 3,812,585 A | * | 5/1974 | Balson | A61C 5/125 433/39 |
| 4,824,365 A | * | 4/1989 | von Weissenfluh | A61C 5/125 433/39 |
| 5,055,045 A | * | 10/1991 | Dickie | A61C 5/125 433/155 |
| 5,501,595 A | * | 3/1996 | Brorson | A61C 5/125 433/39 |
| 5,584,692 A | * | 12/1996 | Weissenfluh | A61C 5/125 433/155 |
| 6,079,978 A | * | 6/2000 | Kunkel | A61C 5/125 433/149 |
| 6,234,793 B1 | * | 5/2001 | Brattesani | A61C 3/06 433/149 |
| 6,749,429 B1 | * | 6/2004 | Haraden | A61C 5/125 433/39 |
| 8,517,732 B2 | * | 8/2013 | Segal | A61C 5/125 433/155 |
| 2005/0221255 A1 | * | 10/2005 | Haraden | A61C 5/125 433/39 |
| 2009/0142725 A1 | * | 6/2009 | Bryant | A61C 5/125 433/39 |
| 2011/0189629 A1 | * | 8/2011 | Kilcher | A61C 5/125 433/39 |

* cited by examiner

CIRCUMFERENTIAL MATRIX BAND

CROSS-REFERENCE TO RELATED APPLICATIONS

This application claims the priority to New Zealand Application No. 593353, filed Jun. 9, 2011, New Zealand Application No. 595654, filed Oct. 10, 2011, and New Zealand Application No. 596177, filed Nov. 3, 2011, the entire contents of which all are hereby incorporated by reference.

FIELD OF THE INVENTION

The present invention relates to a dental matrix band, and in particular, a circumferential dental matrix band for use in restoring a tooth.

BACKGROUND OF THE INVENTION

Circumferential matrix bands and the use of matrix bands are well known and widely utilized in restorative dentistry.

The main problem with the prior art is that circumferential bands either require tensioners to be left in place during the restoration procedure to retain the tension on the matrix band, or the band is tensioned into a barrel-type feature. In both cases the restoration procedure is restricted by the presence of the tensioning device.

A dental matrix retainer is a mechanical device that clamps the matrix band and fixes it around the tooth during tooth restoration. It usually consists of a main body element and a head element. The matrix band is fitted through the head element and the main body provides for the tightening of the matrix band around the tooth. As suggested above, the problem with the prior art is that matrix band retainers are left attached to the circumferential band during the restoration and are a source of interference to the dentist.

SUMMARY OF THE INVENTION

It is an object of the present invention to provide a circumferential matrix band which is easy to tension.

It is a further object of the present invention to include a circumferential matrix band which once placed, offers less obstruction in the restoration area.

It is still a further object of the present invention to provide a means of easily placing and tightening a circumferential band around a tooth.

The present invention therefore provides a dental matrix band which includes a band having a first end and a second end. The band is folded over with the first end and second end generally aligned. A portion of the band adjacent the first and second ends form opposed facing band portions in contact with one another, and another portion of the band forming a looped band forming a circumference. A first or stationary toggle is secured to the band at the first and second ends with the first toggle stationary with respect to the band. A second or movable toggle is formed over the band and is capable of sliding over the opposed facing band portions in contact with one another, whereby sliding of the movable toggle away from the first and second ends causes the circumference of the looped band to reduce in size.

The dental matrix may include one or more generally vertical rows of perforations which allow detachment of a portion of the band after the band has been secured about the tooth to be restored. In addition, the band may include one or more holes adjacent the perforations to assist in manipulating the band and to assist in tearing the band along the perforations. The looped band may include a top tab to assist in removing the looped band from the tooth after the restoration is complete. The top tab may include a hole for manipulation. One or more vertical rows of perforations may be associated with the top tab to allow tearing of the looped band after the restoration is complete and the looped band is to be removed. Through holes may also be provided adjacent the stationary toggle to assist in manipulation of the band, such as during placement of the band within the mouth. Tabs may extend from a bottom edge of the band and arranged to be aligned with the inter-proximal spaces once the band is fixed in place. Thereafter, wedges may be inserted on either side of the tooth under restoration to ensure the matrix band is in secured contact with the tooth.

DETAILED DESCRIPTION OF THE INVENTION

Figure 1:
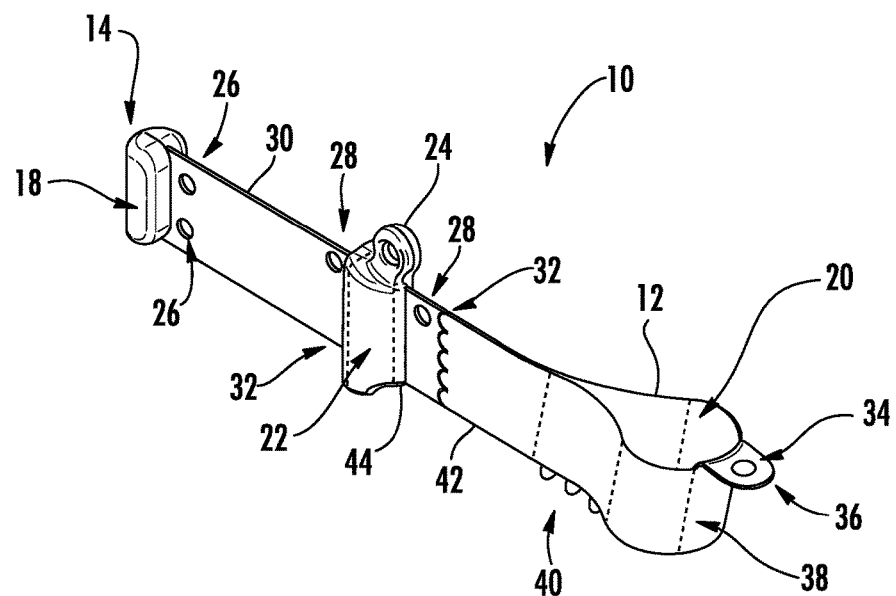
FIG. 1 is a perspective view of a circumferential dental matrix band in accordance with one embodiment of the present invention.
Figure 2:
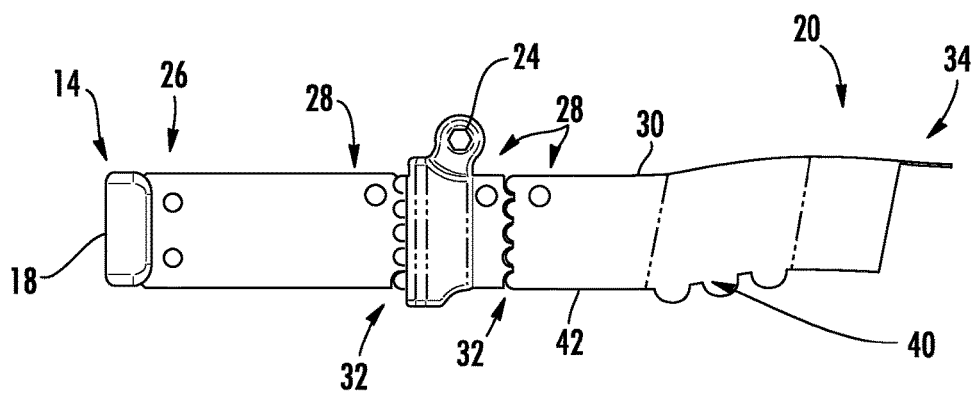
FIG. 2 is a side view of the circumferential dental matrix band of FIG. 1 in accordance with the present invention.

FIGS. 1 and 2 show a first embodiment of the circumferential dental matrix band 10 of the present invention. The circumferential dental matrix band 10 is shown to include a generally elongated metal band 12 having two ends 14. The ends 14 may include a tab portion 15 (see FIG. 3). One of more holes 16 (see FIG. 3) are provided at each of the ends 14. The elongated band 12 is folded back on its self so that the ends 14 meet and the respective one or more holes 16 are aligned. In this configuration, a first toggle 18 is molded over the ends 14 of the elongated band 12 and within the one or more holes 16. The ends 14 are thus secured in place and form a looped band 20 defining a circumference. A second toggle 22 is molded over the matrix band 10. However, the second toggle 22 is not molded within or through any holes in the matrix band 10. Rather, the second toggle 22 is molded in a manner to allow the second toggle 22 to slide along the matrix band 10. One embodiment considers an interference fit which allows movement of the toggle under force exerted by instrument or a mechanism such as a retainer. In the event wedges are utilized, the movable toggle may be provided to move with less force exerted in comparison where a wedge is not contemplated. As the second or movable toggle 22 slides away from the first or stationary toggle 18 in a direction towards the looped band 20, it will be appreciated that the movable toggle 22 is capable of reducing the size of the circumference formed by the looped band 20. An optional hole 24 may be provided in the movable toggle 22 to accommodate manipulation of the movable toggle 22 with an instrument such as a pin-tweezer (not shown).

The circumferential dental matrix band 10 includes one or more holes 26 adjacent to the one or more holes 16. It will of course be understood that the one or more holes 26 are formed by pairs of one or more holes, the pair of holes being aligned with one another in a manner similar to the arrangement of the holes 16. Similarly, the circumferential dental matrix band 10 is provided with one or more holes 28 provided along a top edge 30 of the circumferential dental matrix band 10 on one or both sides of vertical rows of perforations 32.

FIGS. 1 and 2 further show one or more rows of vertical perforations 32 on the matrix band. The perforations may take a variety of forms which allow tearing under force exerted by the dentist, such as via pin tweezers or similar instrument. A top tab 34 with a hole 36 is provided at the looped band 20. The tab 34 defines a width. One or more vertical rows of perforations 38 are provided at the looped band 20 and are generally aligned with the width of the top tab 34 or otherwise associated with the top tab 34. One or more pairs of tabs 40 are arranged along the bottom edge 42 of the elongated band 12 within the area of the looped band 20. The pairs of tabs 40 may be opposite and facing each other.

Figure 3:
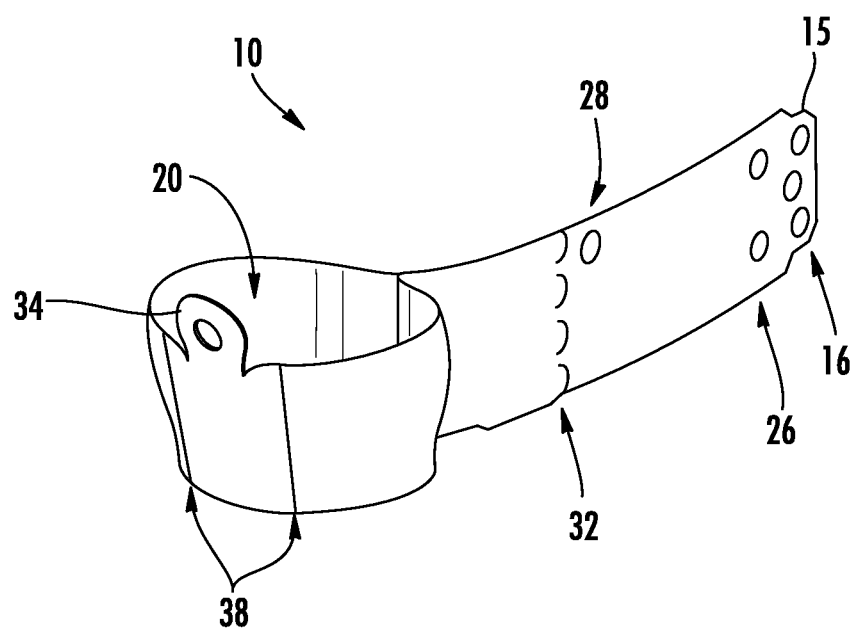
FIG. 3 is a perspective view of a circumferential dental matrix band in accordance with another embodiment of the present invention.

FIG. 3 shows another embodiment of a circumferential dental matrix band 10 wherein the toggles have been omitted to show other features. FIG. 3 shows the joined ends 14 having the tab portion 15 with the holes 16. As can be seen, the looped band 20 has a non-cylindrical shape, and is substantially conical in shape, wherein the lower portion of the looped band 20 provides a smaller circumference in comparison to the upper portion of the looped band 20.

In addition, the movable toggle 22 of the band 10 includes an edge 44 facing the looped band 20. The edge 44 shown extends substantially vertical. However, the edge 44 may also be formed having either a concave or convex shape, or a sloping profile extending from one or the other direction between the top edge 30 and bottom edge 42. Such configurations allow greater flexibility in conforming with the tooth. In addition, the movable toggle 22 may be broader at the base than the upper portion.

The generally elongated metal band 12 is not limited to a solid material with a straight edge matrix band. The band may be shaped or coated with materials, for example.

In use, if a tensioner mechanism is used, the joined ends 14 of the elongated band 12 are fitted into a Tofflemire-type tensioner or other type of tensioner mechanism, with the sliding or movable toggle 22 positioned in front of the tensioning mechanism. The movable toggle 22 is initially displaced from the looped band 20 with the size of the circumference formed by the looped band 20 being the greatest. The looped band 20 is placed about the tooth (not shown) to be restored. Preferably, the looped band 20 is placed around the tooth to be restored with the stationary toggle 18 extending away from the tooth at approximately a right angle to the buccal portion of the tooth. However, other orientations are contemplated and, in fact, necessary, such as may be dependent on the location of the tooth being restored. The movable toggle 22 is then displaced along the circumferential dental matrix band 10 in a direction toward the looped band 20. The movable toggle 22 is advanced using the Tofflemire-type tensioner or by manipulating the movable toggle 22 with an instrument such as pin tweezers which might engage the hole 24, to slide the movable toggle 22 along the band. As the movable toggle 22 advances towards the looped band 20, it will be appreciated that the size of the circumference formed by the looped band 20 is continuously reduced. As the movable toggle 22 advances, the looped band 20 will close upon the tooth until the movable toggle 22 fits snuggly against the tooth. Any of the holes 26, 28 or 36 may be grabbed by an instrument, such as pin tweezers (not shown) in order to manipulate the band 10.

Wedges (not shown) are then inserted on either side of the tooth to be restored to ensure a tight contact. If the circumferential dental matrix band 10 includes tabs 40 arranged along the bottom edge 42, the tabs 40 are positioned to correspond with the inter-proximal spaces of the teeth. The tabs 40 will be trapped by the wedges and the band 10 is firmly held in position.

The free end of the circumferential dental matrix band 10 formed by the ends 14 is removed by grabbing the band 10 by the holes 28 provided along the top edge 30 with an instrument such as pin tweezers (not shown), and detaching the free end along one of the rows of vertical perforations 32. The resulting detached end of the band 10 is removed from the mouth. The tooth is then restored, as required. Once the restoration is complete, the band 10 can easily be removed from the restored tooth by placing pin tweezers in the hole 36 of the top tab 34 and tearing the band 10 along the one or more vertical rows of perforations 38 to release the band 10 from the tooth.

While the present invention has been described in connection with a specific application, this application is exemplary in nature and is not intended to be limiting on the possible applications of this invention. It will be understood that modifications and variations may be effected without departing from the spirit and scope of the present invention. It will be appreciated that the present disclosure is intended as an exemplification of the invention and is not intended to limit the invention to the specific embodiments illustrated and described. The disclosure is intended to cover, by the appended claims, all such modifications as fall within the scope of the claims.

I claim:

1. A dental matrix band comprising:
   a band having a first end and a second end, wherein the band is folded over with the first end and second end generally aligned, and wherein a portion of the band adjacent the first and second ends form opposed facing band portions in contact with one another, and another portion of the band forms a looped band having a circumference;
   a stationary toggle secured to the band at the first and second ends with the stationary toggle stationary with respect to the band;
   at least two or more generally vertical rows of perforations located opposite one another along the opposed facing band portions in contact with one another; and
   a movable toggle formed over the band, wherein the movable toggle is configured to slide over the opposed facing band portions in contact with one another to a position on the band located between the two or more generally vertical rows of perforations and the looped band, and wherein the movable toggle is a molded structure encircling the band and providing a slidable interference fit with the band, whereby sliding of the movable toggle away from the first and second ends causes the circumference of the looped band to reduce in size,
   wherein the perforations are a point of tearing of the matrix band before restoration when the stationary toggle is in place and the movable toggle is between the two or more generally vertical rows of perforations and the looped band.

2. The dental matrix band of claim 1, further comprising one or more holes at the first end and second end, wherein the holes are aligned in pairs and form respective through holes, and wherein the stationary toggle includes a portion which extends through the through hole to aid in maintaining the stationary toggle in place.

3. The dental matrix band of claim 2, wherein the stationary toggle is molded over the band.

4. The dental matrix band of claim 1, wherein the band includes a top edge, and one or more holes is located near the top edge adjacent to one or more of the vertical rows of perforations.

5. The dental matrix band of claim 1, wherein the looped band includes a top tab.

6. The dental matrix band of claim 5, wherein the top tab includes a hole.

7. The dental matrix band of claim 5, further comprising one or more vertical rows of perforations associated with the top tab.

8. The dental matrix band of claim 1, further comprising one or more tabs arranged to be generally aligned with inter-proximal spaces associated with a tooth to be restored.

9. The dental matrix band of claim 1, further comprising one or more holes at the first end and second end, adjacent the stationary toggle in a direction towards the looped band, whereby the band may be manipulated with the use of an instrument.

10. The dental matrix band of claim 1, wherein the movable toggle includes a handle, whereby the movable toggle may be manipulated with the use of an instrument.

11. The dental matrix band of claim 1, wherein the movable toggle includes a hole, whereby the movable toggle may be manipulated with an instrument.

12. The dental matrix band of claim 1, wherein the band is made of metal.

13. The dental matrix band of claim 1, wherein the movable toggle includes an edge facing the looped band, and the edge is vertical.

14. The dental matrix band of claim 1, wherein the movable toggle includes an edge facing the looped band, and the edge includes a concave shape.

15. The dental matrix band of claim 1, wherein the movable toggle includes an edge facing the looped band, and the edge includes a convex shape.

16. The dental matrix band of claim 1, wherein the movable toggle includes a top portion and a base portion, and the base portion is broader than the top portion.

17. The dental matrix band of claim 1, wherein the band is made from a generally rectangular shaped band.

18. The dental matrix band of claim 1, wherein the looped band forms a non-cylindrical shape.

19. The dental matrix band of claim 1, wherein the looped band is tapered such that one end has a circumference that is smaller than a circumference at another end.

20. The dental matrix band of claim 1, wherein the looped band has a substantially conical shape.

* * * * *